(12) United States Patent
Gwen

(10) Patent No.: US 6,766,808 B2
(45) Date of Patent: Jul. 27, 2004

(54) DENTAL FLOSS HOLDER AND METHOD OF MAKING A DENTAL FLOSS HOLDER

(76) Inventor: Patrick Gwen, 3443 Leeland, Houston, TX (US) 77003

( * ) Notice: Subject to any disclaimer, the term of this patent is extended or adjusted under 35 U.S.C. 154(b) by 0 days.

(21) Appl. No.: 10/189,727

(22) Filed: Jul. 3, 2002

(65) Prior Publication Data

US 2004/0003827 A1 Jan. 8, 2004

(51) Int. Cl.[7] .............................................. A61C 15/00
(52) U.S. Cl. ..................................................... 132/323
(58) Field of Search .......................... 433/141; 264/274, 264/273, 243; 132/323–327

(56) References Cited

U.S. PATENT DOCUMENTS

| | | | |
|---|---|---|---|
| 2,187,899 A | * 1/1940 | Henne | 132/323 |
| 3,783,883 A | * 1/1974 | Alexander | 132/323 |
| 3,926,201 A | * 12/1975 | Katz | 132/323 |
| 4,006,750 A | 2/1977 | Chodorow | |
| 4,013,085 A | * 3/1977 | Wright | 132/323 |
| 4,655,233 A | * 4/1987 | Laughlin | 132/323 |
| 4,817,642 A | * 4/1989 | Lipp | 132/324 |
| 5,053,178 A | * 10/1991 | Butlin et al. | 264/254 |
| 5,538,023 A | 7/1996 | Oczkowski et al. | |
| 6,065,479 A | 5/2000 | Chodorow | |
| 6,102,051 A | * 8/2000 | Neves | 132/321 |

* cited by examiner

Primary Examiner—Kevin Shaver
Assistant Examiner—Stephanie Willatt
(74) Attorney, Agent, or Firm—Law Office of Tim Cook PC

(57) ABSTRACT

A dental floss holder comprises a generally planar handle with a pair of spaced apart arms adapted to retain a length of dental floss tape. By forming the holder in a single plane, the holder is inexpensive to manufacture. Dental floss tape is molded into the arms at an angle. The holder is injection molded to include a pair of spaced apart posts formed as an integral part of the arms, thereby forming a positive mount for the tape in the holder.

4 Claims, 1 Drawing Sheet

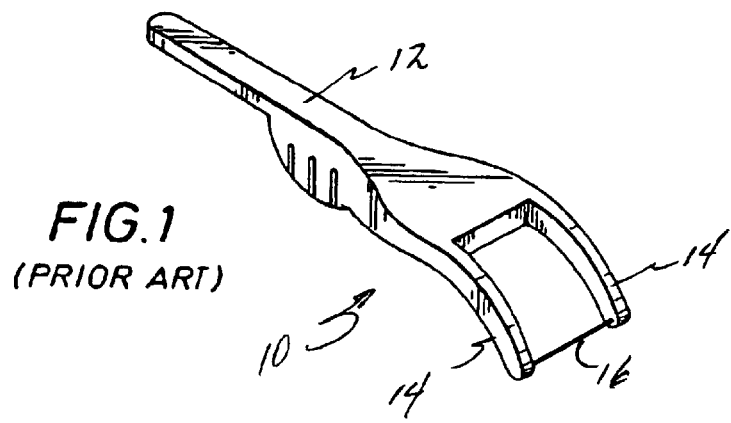
FIG. 1
(PRIOR ART)
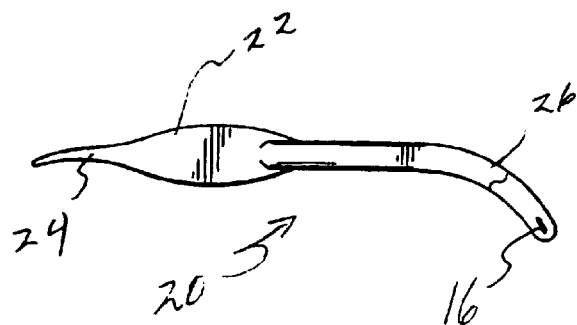
FIG. 2
(PRIOR ART)
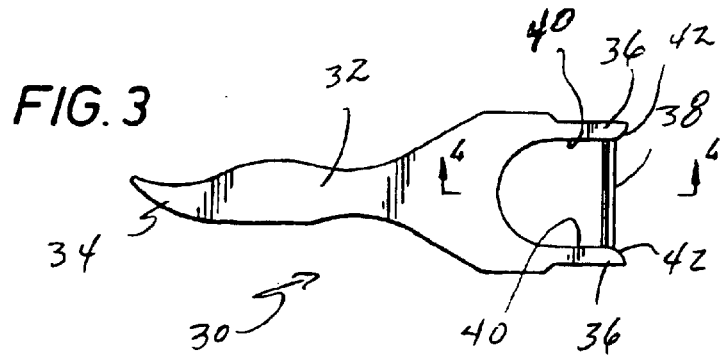
FIG. 3
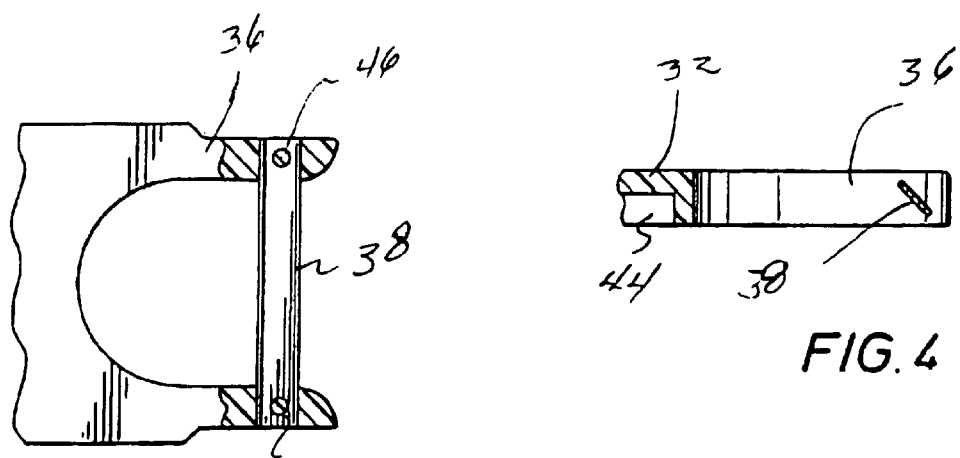
FIG. 4
FIG. 5

DENTAL FLOSS HOLDER AND METHOD OF MAKING A DENTAL FLOSS HOLDER

FIELD OF THE INVENTION

The present invention relates generally to the field of disposable dental floss holders, and, more particularly, to an injection molded, planar dental floss holder adapted to retain a length of flat dental floss at an angle to the plane of the holder. The present invention also relates to a method of making such a holder.

BACKGROUND OF THE INVENTION

The dental floss holder of the present invention finds application in the field of dental care, whether for the use of dentists and dental hygienists, or for personal use. The holder retains a length of dental floss for removing plaque from tooth surfaces and food particles from between teeth.

As described in U.S. Pat. No. 5,538,023, in the past, teeth have been cleaned primarily by brushing, and the spaces between teeth have been cleaned by a variety of methods including brushing, water jets of water, toothpicks, and the like. The spaces between teeth have often been cleaned by the manual application of floss and dental tape or similar thread.

The objective in cleaning teeth is to remove food particles, chemicals, and plaque from tooth surfaces. Secondarily, the objective in cleaning teeth is to freshen the breath, often fouled by foreign matter on and between the teeth. However, even when plaque is removed, it can reform within a relatively short period of time. Thus, the regular removal of such plaque is an essential part of dental health.

If plaque is not removed daily, it can develop and harden into firmly attached tartar which may cause a variety of dental maladies, including gingivitis, and ultimately tooth loss. Unfortunately, brushing alone is not effective to remove plaque from surfaces between teeth. Of the available method of tooth care, only dental floss is effective for removing plaque from between teeth. Floss is typically a strand of multi-filament nylon, either round or flat, that is moved into the space between the sides of two teeth. However, positioning and maneuvering floss is difficult at best. The procedure for using floss today most often includes winding opposite ends of a strand around one finger of each hand respectively, then inserting these two fingers into one's mouth, attempting to position the span of floss between the fingers in the desired location, and finally reciprocating the floss between teeth while also moving it vertically along the tooth from tip to gum.

This technique for the use of floss is so tedious that even folks who are serious about dental hygiene seldom floss daily. Attempts have been made to render flossing less tedious and more effective by the development of holders onto which floss is attached. Most holders have two arms across which the floss is strung. However, such holders have been less than ideal and have not resulted in the increased use of dental floss.

Various holders proposed in the art have been directed to ease of use of both round, multi-stranded floss and floss tape. The present invention is specifically directed to the art of holder for floss tape. One of the innovations in the art has resulted in the use of floss tape including TEFLON®. Typically, the tape is laid across an injection mold during the molding process, the holder is formed around the tape, and the ends of the tape are cut or burned off to remove the excess tape extending beyond the arms of the holder. However, one of the common drawbacks of this structure is that the tape tends to pull our of the holder, rendering the floss holder unusable.

Another recognized need in the art is that of orienting the tape so that it can be easily slipped into the space between the teeth. Since the tape is flat, it should be oriented in the same direction as the space between the teeth, i.e. generally perpendicular to the gums. Once such proposed solution involves curving the spaced-apart arms holding round, multi-stranded floss in a downward direction toward the teeth, such as that depicted in FIG. 1, described below. A proposed solution for a holder of flat dental floss also includes curving the arms toward the teeth, and orienting the flat tape generally parallel to the ends of the arms, such as that depicted in FIG. 2. Both solutions have been somewhat successful, but the cost of manufacturing both holders is unnecessarily high due to the shape and orientation of the holder. Further, neither holder solves the solution of the floss pulling out of the arms of the holder.

Thus, there remains a need in the art for a dental floss tape holder which is simple and inexpensive to manufacture, but is easy to use so as to encourage its frequent use. Also, the holder should firmly retain the floss within the holder.

SUMMARY OF THE INVENTION

The present invention is directed to solving these and other drawbacks in the art. The holder of this invention is a generally planar, disposable floss holder with a pair of spaced apart arms adapted to retain a length of dental floss tape. By forming the holder in a single plane, unlike the curved aspect of the holders of FIGS. 1 and 2, the holder is much less expensive to manufacture. In order to orient the floss tape at a convenient angle for insertion between teeth, the flat floss is molded into the arms at an angle. In this way, by angling the holder within one's mouth, the user can easily insert the floss tape between teeth, while providing an abrasive surface with which to floss the plaque from tooth surfaces.

The present invention also provides a method of making the dental floss tape holder described above. In order to eliminate the tendency of the tape to pull out of the arms of the holder, a pair of spaced apart holes are formed in the tape before the tape is laid on the injection mold. When the plastic is injected into the hold, the plastic flows through the holes, and then the plastic hardens, thereby forming a positive mount for the tape in the holder.

These and other features and advantages of this invention will be readily apparent to those skilled in the art.

BRIEF DESCRIPTION OF THE DRAWINGS

So that the manner in which the above recited features, advantages and objects of the present invention are attained and can be understood in detail, more particular description of the invention, briefly summarized above, may be had by reference to embodiments thereof which are illustrated in the appended drawings.

FIG. 1 is a perspective view of a known dental floss holder, illustrating the curved arms for such a holder.

FIG. 2 is a side view of another known dental floss holder, also showing curved arms, as well as the dental floss tape oriented parallel to the arms of the holder.

FIG. 3 is top view of the dental floss holder of the present invention.

FIG. 4 is a side detail view of the holder of this invention in partial section taken along section lines 4—4 of FIG. 3, illustrating the angled dental floss tape.

FIG. 5 is a top detail view in partial section illustrating the molded posts of the invention, adapted to retain the floss tape.

DETAILED DESCRIPTION OF A PREFERRED EMBODIMENT

FIGS. 1 and 2 depict known dental floss holders having drawbacks which are addressed by the present invention. FIG. 1 shows a holder 10 comprising a handle 12 and a pair of spaced-apart arms 14. The arms retain a length of floss 16 strung tautly between them. The arms 14 are curved downwardly to assist in the insertion of the holder into the user's mouth, thereby providing a relatively large profile. Such a large profile unnecessarily increases the cost of manufacture of the holder 10. Further, one of the recognized drawbacks of the holder of FIG. 1 is the tendency of the floss to pull out of one arm or the other as the floss 16 is forced between two closely spaced teeth.

These drawbacks in the art are not solved, or even addressed by the known holder illustrated in FIG. 2. FIG. shows a holder 20 comprising a handle 22, including an integrally formed tooth pick 24 and arms 26, only one of which is visible in FIG. 2, formed in a manner similar to at illustrated in FIG. 1. However, the holder 20 retains a quantity of dental floss tape 16 oriented parallel to the arms 26. Further, the arms are curved, once again presenting a relatively large profile aspect, thereby increasing the cost of manufacture. There is also no means of positively retaining the tape 28 within the arms of the holder, and the tape thus tends to pull out of the arms during use.

These and other problems in the art are solved by the present invention as shown in FIGS. 3 through 5. In one aspect, the invention is a holder 30 comprising a handle 32 with an integrally formed tooth pick 34. The pick portion of the holder is molded with a much thinner profile than the handle for flexibility, to facilitate its use, and to reduce the amount of material required for the manufacture of the holder 30.

Extending from the handle 32 are two spaced-apart arms 36 adapted to retain a quantity of dental floss tape 38. The arms 36 define opposing faces 40 which define rounded corners 42, another feature of this invention, to reduce the injury to gums as the floss holder is moved back an forth in a reciprocating action. Note also that the arms 36 and the pick 34 lie in the plan of the handle, unlike the pick 24 of FIG. 2. This feature of the invention also reduces the manufacturing costs of the holder 30.

As shown in FIG. 4, he floss 38 is retained between the arms 36 at an angle to the plane of the holder, preferably at about 45°, but may lie in any convenient angle between about 30° and approaching 90°, for ease of use of the holder. If the floss is placed at an angle less than 30° from the plane of the holder, then the holder must be cocked at an uncomfortable angle in order to insert the tape 38 between two closely-spaced teeth.

The holder 30 also defines a cavity 44 on the underside of the handle 32, reducing the amount of material required to form the holder, and proving flexibility to the holder as a whole.

Finally, referring now to FIG. 5, a further aspect of the manufacture of the holder 30 is shown. The holder 30 is preferably injection molded and, prior to injection of the plastic which forms the holder, the tape 38 is laid across the mold. The tape 38 has a hole formed at the junction of the tape and the arm 36 on either side so that, when the plastic is injected into the mold, a post 46 is formed as an integral part of each arm. The post firmly retains the tape within the arm, and eliminates the tendency of the tape to pull out of the arm during use.

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

I claim:

1. A dental floss holder comprising:
  a. a handle defining a plane;
  b. a pair of space apart arms integrally formed with the handle in the plane of the handle, one of the pair of arms defining a first post and the other of the pair of posts defining a second post; and
  c. a length of flat dental floss tape molded into and extending between the arms, the tape lying in a tape plane which is at a non-zero angle from the plane of the handle, the tape having a first hole therethrough to receive the first post and a second hole therethrough to receive the second post.

2. The dental floss holder of claim 1, wherein the arms define opposing faces, each of the opposing faces having a rounded corner adjacent the tape.

3. The dental floss holder of claim 1, further comprising a tooth pick integrally formed with the handle and lying in the plane of the handle.

4. The dental floss holder of claim 1, further comprising a cavity formed in the handle.

* * * * *